[19] United States Patent
Mann et al.

[11] 4,454,871
[45] Jun. 19, 1984

[54] ANKLE-FOOT ORTHOSIS
[75] Inventors: Irwin Mann, Lake Orion, Mich.; Richard L. Hecker, Milwaukee, Wis.
[73] Assignee: Med-Con, Inc., Downers Grove, Ill.
[21] Appl. No.: 420,744
[22] Filed: Sep. 21, 1982

Related U.S. Application Data
[63] Continuation of Ser. No. 191,675, Sep. 29, 1980, abandoned.

[51] Int. Cl.³ .............................................. A61F 5/04
[52] U.S. Cl. .............................. 128/80 H; 128/89 R; 128/90
[58] Field of Search .................. 128/80 R, 80 H, 83.5, 128/89 R, 90, 165, 166

[56] References Cited
U.S. PATENT DOCUMENTS
3,802,424  4/1974  Newell ............................. 128/83.5
3,814,088  6/1974  Raymond ......................... 128/80 H
3,871,367  3/1975  Miller .............................. 128/89 R Primary Examiner—Paul J. Hirsch
Attorney, Agent, or Firm—Burton, Parker & Schramm

[57] ABSTRACT

An easily removable ankle-foot orthosis 11 is formed by molding an inner liner of plastazote foam 24 and an outer layer of polypropylene gel 25 to a positive shaped mold 10 of the foot 12 and lower leg 14. The positive mold includes a pair of opposed protruding longitudinal ribs 18, 20 disposed alongside the lateral and medial surfaces of the lower half of the leg to below the ankle. The resulting orthosis, which comprises an open-toed boot-shaped structure formed having a continuous longitudinal frontal opening 46, is adapted for securely maintaining the foot and leg of a wearer in a slightly less than 90° relationship to one another, the rigidity of the orthosis being enhanced by the longitudinal ribs formed therein. The orthosis is easily removable through use of the frontal opening and may include a plurality of transverse binding straps 50 for snugly fitting a single orthosis to a variety of foot and leg sizes.

6 Claims, 5 Drawing Figures

ANKLE-FOOT ORTHOSIS

This application is a continuation of application Ser. No. 191,675, filed Sept. 29, 1980 now abandoned.

DESCRIPTION

BACKGROUND OF THE INVENTION

The present invention relates generally to an ankle-foot orthosis and, more particularly, to an easily removable ankle-foot orthosis adapted for limiting range of motion of the ankle joint, subtalar joint and midtarsal joints of the foot while maintaining a relative approximately 90° relationship between the foot and leg.

The ankle joint, that joint formed by the articulation of the inferior surfaces of the tibia and fibula with the superior, medial and lateral surfaces of the talus, and the subtalar joint, that joint formed between the inferior surface of the talus and superior surface of the calcaneus bones of the foot are primarily effected by limited ranges of motion. The ranges of motion that occur are in the cardinal body planes, transverse, frontal and sagital, and are in varying degrees. The forces which initiate motion, which are muscle function and other biomechanical influences, are altered by the orthosis to accomplish the limited range of motion.

It is necessary at various times to limit ankle joint and subtalar joint motion as described above. For example, it is normally necessary to limit movement of the ankle joint and subtalar joint to promote healing thereof after surgery or bone fusion, after minor injuries such as bone fractures and ligament strains and to compensate for certain neuro muscular or musculo-skeletal disorders such as dropfoot and for inflammatory disease of tendons, tendon separations and other soft tissue disorders. Also, limitation of the ankle joint and subtalar joint if frequently prescribed for treating certain arthritic conditions. A device for limiting movement of the ankle joint and subtalar joint is referred to as an ankle-foot orthosis, the device having as its primary function that of maintaining the foot and leg in a substantially 90° relationship to one another.

Prior art ankle foot orthosis have taken a number of different forms. Conventionally, plaster casts, metal bracings and other synthetic products as fiber casts, have been used to immobilize the ankle joint to promote healing. In addition, since the devices are not readily removable, the wearer cannot bath nor ambulate conveniently. More recently, vacuum forming and extrusion molding techniques have been used to custom make polypropylene total contact orthosis. The present invention is lighter in weight and easier to apply than plaster casts and metal bracings. The orthosis facilitates immediate ambulation after application. The device allows quick removal and re-application in order to facilitate clinical evaluation and physical therapy. This invention will utilize for the most part there fabricating techniques to produce this foot and ankle orthosis.

SUMMARY OF THE INVENTION

The ankle-foot orthosis 11 of the present invention is formed by wrapping a sheet of plastazote (a foamed plastic) 24 partially about a positive mold 10 having a foot portion 12, an ankle-joint portion 14 and a leg portion 16. A layer of polypropylene gel 25 is applied overlying the sheet of plastazote foam whereupon a vacuum molding process is employed to mold the plastazote foam and polypropylene gel to the positive cast, previously described, to obtain foot and ankle orthosis shell. This shell with its modification, to be described, will be utilized by the wearer so as when applied properly will create limited ankle and subtalar joint motion. Since the plastazote foam was only partially wrapped about the positive mold, a continuous longitudinal opening is formed in the orthosis extending adjacent the dorsal surface of the foot and anterior surface of the leg of the wearer for facilitating convenient removal thereof. Binding straps are provided for partially closing the opening and snugly fitting the orthosis to the wearer. Also, the orthosis is formed having a pair of opposed exteriorly protruding longitudinal ribs for reinforcing the rigidity of the polypropylene layer for inhibiting flexion of the wearer's ankle joint.

DESCRIPTION OF THE PREFERRED EMBODIMENT

Figure 1:
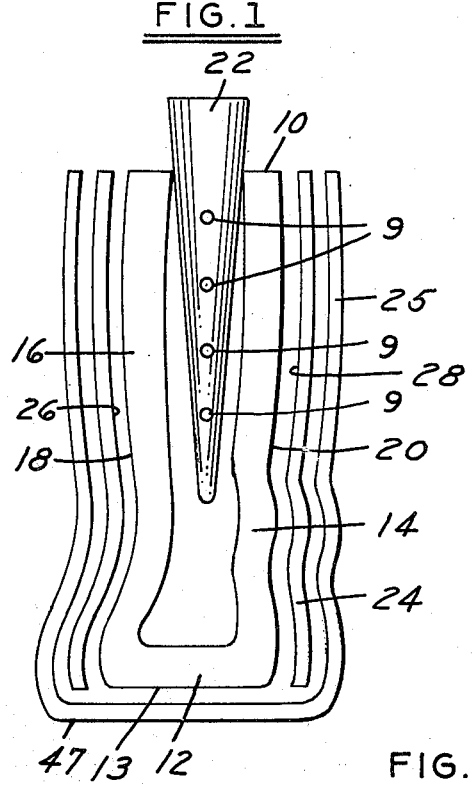
FIG. 1 is a front elevation view of the mold for manufacturing with the major components of the orthosis.
Figure 2:
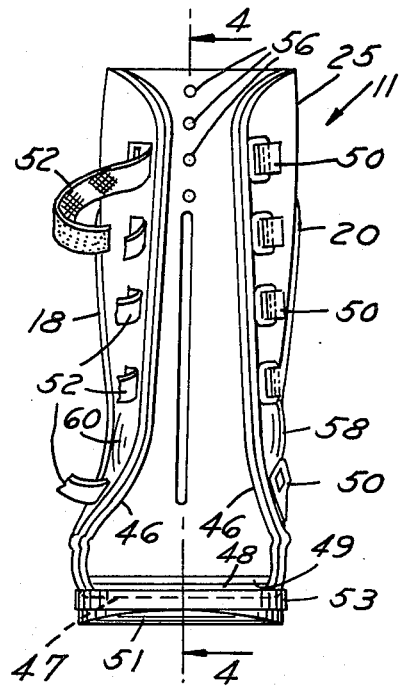
FIG. 2 is a front elevation view of the ankle-foot orthosis of the present invention.
Figure 3:
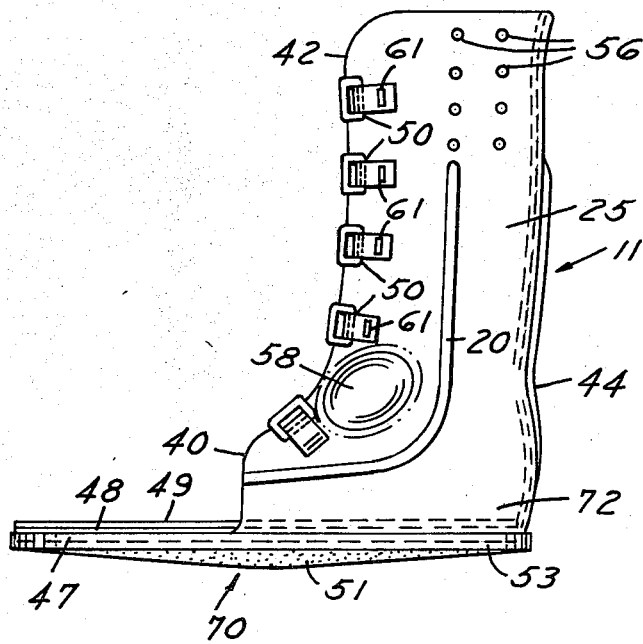
FIG. 3 is a side elevation view of the ankle-foot orthosis of the present invention.
Figure 4:
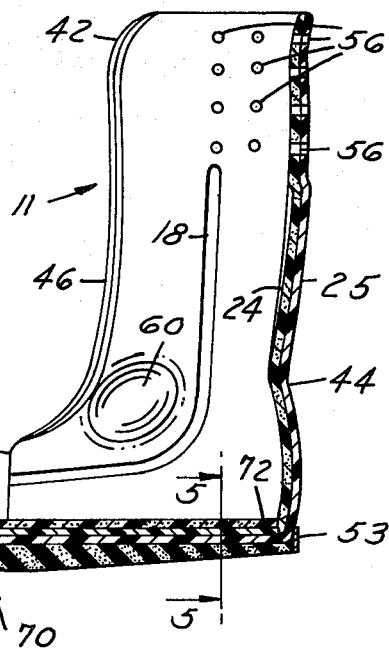
FIG. 4 is a cross-sectional view of the orthosis taken along lines 4—4 of FIG. 2.
Figure 5:
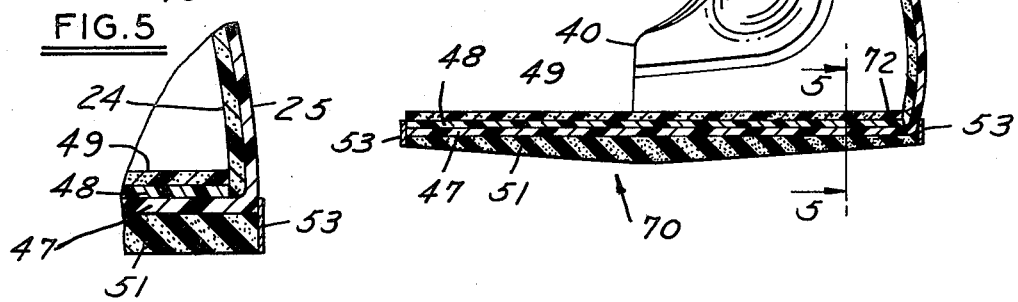
FIG. 5 is a cross-sectional view of the orthosis taken along lines 5—5 of FIG. 4.

Referring now to the drawing and, in particular, to FIG. 1, there is illustrated a positive mold 10 having a boot-like shape and including a foot portion 12, an ankle-joint portion 14 and a leg portion 16 closely simulating the foot, ankle-joint and leg of a human being. The positive mold 10 is constructed such that the longitudinal axis of the foot portion 12 is substantially in a 90° relationship with the longitudinal axis of the leg portion 16 and includes a pair of opposed protruding longitudinal ribs 18 and 20 disposed along side the lateral and medial surfaces of the ankle-joint portion 14. The mold 10 may be constructed of a number of different materials such as fiberglass reinforced plaster, plastic resined cork or metals, etc. A metal tube 22 is positioned down the center section of mold 10 and holes 9 are drilled through the frontal portion of mold 10 into the corresponding metal tube. The proximal portion of tube 22 is attached to an apparatus (not shown) used to create a suction through the tube and thusly creating a vacuum to the plastazote liner 24 and gelatinous polypropylene 25 as it is wrapped around the mold. The plastazote is wrapped from 26 around the back portion of the mold to point 28 which allows for the guideline of where the frontal opening will be. The gelled polypropylene is wrapped completely around the mold 10, both leg, foot and ankle portions, and gathered in front and top to create a closed system for vacuum molding process. To obtain the polypropylene into its gel like flexible form, a sheet of polypropylene (such as that available from GTR Plastic Film Company of New Commerce, Ohio) is cut so that its diameter when placed on the mold will be greater than the circumference of the mold, and is heated in an oven between 400° to 500° F. for 5–10 minutes.

The ankle-foot orthosis formed according to the above described process is illustrated in detail in FIGS. 2–5. It will be observed that the orthosis comprises a generally open-toed boot-shaped structure having a foot portion 40, a leg portion 42 and an ankle-joint portion 44 all consisting of the inner plastazote liner 24 and the outer polypropylene layer 25. The orthosis is further characterized by a continuous longitudinal opening 46 extending adjacent the dorsal surface of the foot and the anterior surface of the leg of a wearer. A bottom foot portion 47 comprises a continuation of the outer polypropylene layer to provide support for the foot and toes of the wearer. A cushioned material which is a laminate of polypropylene 48 with plastazote 49 on top is disposed above the bottom foot portion 47 to provide protection and comfort to the foot of the wearer.

An alternative means of increasing ridigity of the bottom foot portion to limit flexion within the foot is to place a rigid member (not shown) at position 13 at the base of mold 10 beneath the foot portion 12 prior to molding. Any rigid member can be used as wood, metal and the like. It is to be appreciated that as the foot portion is limited in flexion, so, too, is there a limiting of the ankle.

A rubber sole 51 is coupled to the bottom of the orthosis extending the full length of the bottom foot portion 47 having a maximum thickness approximately $\tfrac{3}{8}''-1\tfrac{8}{2}''$ extending from the heel to just behind the ball of the foot and then tapers to the toe. A plurality of binding straps 50 each having one end 61 securely fastened to the orthosis along one side of the opening 46 and a second end adjustably fastenable by the wearer, e.g., by velcro fasteners 52 or the like, to the orthosis along the other side of the opening 46, are provided for snugly fitting the orthosis to the foot of the wearer. Due to the flexibility of the foot and leg portion 40 and 42 of the orthosis, it will be appreciated that the opening 46 provides a convenient facility whereby the orthosis may be easily placed on the foot of the wearer to permit, for example, washing and cleaning of the foot as well as of the device. Moreover, the use of adjustable binding means 50 as straps enable a single orthosis to accommodate a variety of different foot and ankle sizes so that size customizing is not necessary. In fact, it has been found that fabricating the orthosis in four basic sizes will cover the range of most normal foot sizes, i.e., a normal foot size will be suitably accommodated by one of the four basic orthosis sizes.

The rubber sole 51 can be a tapered rippled sole.

A rubber based cover 53 is adhered to the sole portion at the rear and front portion of the foot of the orthosis to improve the appearance thereof.

In addition to being easily placed on and removed from the foot of a wearer, the orthosis also serves to limit movement of the ankle-joint of the wearer by maintaining the wearer's foot and leg in a substantially 90° relationship to one another. The ankle-joint immobilizing characteristics of the orthosis are enhanced by the increased thickness of the polypropylene layer 25 in the ankle-joint portion 44 and by the opposed exteriorly protruding longitudinal ribs 18 and 20 formed in the orthosis and disposed adjacent the lateral and medial surfaces of the ankle-joint of the wearer. In combination, these two reinforcing techniques advantageously limit any possible flexion of the ankle-joint of the wearer to promote rapid healing of an injured ankle-joint or to compensate for various types of disorders which may be affecting the joint.

Additionally, to decrease pressure on a swollen foot and to accommodate the ankle, protrusions 58 and 60 (viewed from the interior of the orthosis) are formed during the molding process.

The leg portion 42 of the orthosis may be provided with a plurality of perforations 56 disposed thereabout. The perforations 56 permit air to enter the orthosis and thereby ventilate the wearer's leg preventing the discomfort which could otherwise result.

It is to be appreciated that a wide variety of vacuum formable plastic films may be used in place of polypropylene. One criteria is an impact strength equal to or exceeding that of a sheet of 3/16" polypropylene.

The formation of the orthosis is made by means of conventional vacuum forming techniques. While well known compression molding techniques can also be used, it is preferred to use vacuum molding techniques.

An important aspect of the present invention is to have a rigid boot portion 70 which is comprised of sole member 51, foot portion 47 and back heel portion 72 constructed so as to cause limitation of motion at ankle and subtalar joints during ambulation of the wearer.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. An easily removable orthosis (11) for maintaining an ankle and a foot in a substantially 90° relationship to one another, said orthosis comprising a generally boot shaped structure including a foot portion (40) and a leg portion (42) disposed in a substantially 90° relationship to one another, said structure being composed of a continuous inner liner of foamed plastic (24) surrounded by a continuous outer layer of vacuum formable plastic film (25), a protrusion in the ankle joint area, the portions of said outer layer adjacent the medial and lateral surfaces of the ankle joint of a wearer being deformed for defining a pair of opposed exteriorly protruding longitudinal ribs (18), (20); said protrusion and ribs reinforce the rigidity of said outer layer for inhibiting flexion of the wearer's ankle joint, said boot shaped structure further including a continuous longitudinal opening (46) extending adjacent the dorsal surface of the foot and anterior surface of the leg of a wearer for facilitating removal of and entrance into said structure and binding means (50) across said opening for snugly fitting said structure to a wearer and having the ability of only partially closing the continuous opening and further having a rigid boot portion (70) placed below the foot portion (40) so as to cause limitation of motion at ankle and subtalar joints during ambulation of the wearer; wherein said foot portion includes a sole means (51) and the sole means varies in thickness and is bio-mechanically designed to allow for a forward motion of the leg over the foot so as not to over-extend the knee in propulsion.

2. An orthosis according to claim 1 wherein the plastic film (25) is comprised of polypropylene layer and wherein the portion of said polypropylene layer adjacent the ankle joint of a wearer is substantially thicker than the remainder of said polypropylene layer.

3. An orthosis according to claim 1 wherein said binding means comprises a plurality of binding means 50 having a first end 61 securely fastened to said structure along one side of said opening and a second end 52 adjustably securably to said structure along the opposite side of said opening for adjustably pulling said sides of said opening toward each other.

4. An orthosis according to claim 3 wherein said leg portion of said structure includes a plurality of perforations 56 disposed thereabout.

5. The orthosis of claim 1 further containing a piece of rigid inner sole placed atop the formed foot portion for maintaining rigidity to, and reducing flexion of, the sole.

6. The orthosis of claim 1 further comprising an increased thickness of the outer layer in the ankle-joint portion to promote ankle-joint immobilization.

* * * * *